United States Patent
Piano et al.

(10) Patent No.: US 12,162,827 B2
(45) Date of Patent: Dec. 10, 2024

(54) ISOLATION OF CHROMOPLASTID CAROTENOIDS FROM FRUITS

(71) Applicant: UNIVERSITA' DEGLI STUDI DI CAGLIARI, Cagliari (IT)

(72) Inventors: Dario Piano, Cagliari (IT); Domenica Farci, Cagliari (IT)

(73) Assignee: UNIVERSITA' DEGLI STUDI DI CAGLIARI, Cagliari (IT)

( * ) Notice: Subject to any disclaimer, the term of this patent is extended or adjusted under 35 U.S.C. 154(b) by 500 days.

(21) Appl. No.: 17/630,130

(22) PCT Filed: Jul. 26, 2019

(86) PCT No.: PCT/IB2019/056397
§ 371 (c)(1),
(2) Date: Jan. 25, 2022

(87) PCT Pub. No.: WO2021/019275
PCT Pub. Date: Feb. 4, 2021

(65) Prior Publication Data
US 2022/0259128 A1 Aug. 18, 2022

(51) Int. Cl.
C07C 45/79 (2006.01)
C07C 7/00 (2006.01)
C07C 7/10 (2006.01)
C07C 7/12 (2006.01)

(52) U.S. Cl.
CPC .............. *C07C 45/79* (2013.01); *C07C 7/005* (2013.01); *C07C 7/10* (2013.01); *C07C 7/12* (2013.01)

(58) Field of Classification Search
CPC .......... C07C 45/79; C07C 7/005; C07C 7/10; C07C 7/12
See application file for complete search history.

(56) References Cited

FOREIGN PATENT DOCUMENTS

| EP | 1423020 | 3/2003 |
|----|---------|--------|
| WO | 9920587 | 4/1999 |
| WO | 2019092387 A1 | 5/2019 |

OTHER PUBLICATIONS

Piano et al. "Characterization under quasi-native conditions of the capsanthin/capsorubin synthase from capsicum annum L" Plant Physiology and Biochemistry, 2019, v 143, p. 165-175.
Wu et al., "The orange carotenoid protein of synchocystis PCC 6803" Biochemica et Biophysica Acta 1322, 1997, p. 1-7.
Farci et al., "S-layer proteins as a source of carotenoids: Isolation of the carotenoid cofactor deinoxanthin from its S-layer protein DR_2577" Food Research International, 2017, v 99, p. 868-876.
Goss et al., "Direct isolation of of a functional violaxanthin cycle domain from thylakoid membranes of higher plants" Planta, 2017, v 245, p. 793-806.

*Primary Examiner* — Sikarl A Witherspoon
(74) *Attorney, Agent, or Firm* — Gregory P. Einhorn; Greer, Burns & Crain, Ltd.

(57) ABSTRACT

The present invention relates to a method for the production of chromoplastid carotenoids that can be isolated from fruits. The procedure of the invention allows to selectively isolate, on the basis of the size (Size Exclusion Chromatography) and in pure form, the carotenoid in the form of regularly shaped and sized aggregates. The process includes the following steps: i) production, in suspension, of homogeneous fragments of the chromoplastidial membranes from the fruits; ii) solution isolation of the membrane components by solubilization with detergents; iii) selective and high-purity isolation of the carotenoid in the form of regular paracrystalline aggregates by a screening technique such as size exclusion chromatography (SEC—Size Exclusion Chromatography).

15 Claims, 1 Drawing Sheet

ISOLATION OF CHROMOPLASTID CAROTENOIDS FROM FRUITS

This application is a national phase application claiming benefit of priority under 35 U.S.C. § 371 to Patent Convention Treaty (PCT) International Application serial number PCT/IB2019/056397, filed Jul. 26, 2019, now pending. The aforementioned applications are expressly incorporated herein by reference in their entirety and for all purposes.

TECHNICAL FIELD

The present invention relates to a method for the production of carotenoids and in particular to the industrial isolation of chromoplastid carotenoids that can be isolated from fruits that contain them. For example purposes we can mention in particular the carotenoid capsorubin, present in the fruits of *Capsicum annuum* red (red pepper), the carotenoid lutein present in the fruits of *Capsicum annuum* yellow (yellow pepper), and the carotenoid lycopene present in *Solanum lycopersicum* (tomato). An equivalent procedure can be used for the isolation of other carotenoids present in the chromoplasts of other varieties of these fruits (e.g. pepper and yellow tomato) and can in any case be extended to any plant species that produces fruits characterized by an accumulation of carotenoids at chromoplastidial level.

This procedure allows you to:
isolate specific carotenoids from natural sources (rather than through synthesis processes);
significantly increase the production offer compared to the potential demand (a limiting factor for this product).

BACKGROUND ART

Carotenoids are antioxidants synthesized by bacteria, algae and higher plants. They have a protective role against oxidative stress induced by chemical or physical factors. These molecules are also essential for animals that, not being able to synthesize them, take them with the diet. Due to the better understanding of their roles and mechanisms in opposing to oxidative stress, the use of carotenoids as dietary supplements, nutraceuticals and drugs for the treatment of various diseases has increased significantly over the last 20 years. This fact has significantly increased the demand for carotenoid-based products on the market, leading this production segment to play a key role in the chemical industry. While a large part of the carotenoids on the market is obtained by chemical synthesis, a growing incidence is due to carotenoids obtained from natural sources in response to the increasingly frequent demand for organic and biological products. Currently, these features suggest that three fundamental criticalities limit the further development of this market: i) exploit new sources of carotenoids; ii) identify and market new types of carotenoids and iii) apply new processes for their industrial isolation from natural sources.

Currently the isolation of capsorubin, and most of the carotenoids present on the market isolated from animal or vegetable matrices, occurs through two ways:

a) a direct way, using production scraps and tares by means of solvents and resulting industrial processing of the extracts obtained in order to obtain a product enriched with variable purities (up to 50-70%; U.S. Pat. Nos. 6,262,284, 6,380,442);

b) an indirect way, semisynthetic and less representative, starting from carotenoid precursors (often destined to the production of highly pure small quantities). The latter is generally associated with greater purities (up to 96%; U.S. Pat. No. 6,262,284).

Currently the availability of capsorubin on the market is significantly limited by the reduced efficiency of the two extraction methods for which methods (a) allows large productions at low cost but also low purity, while method (b) allows high purity but very limited productions and high costs. Furthermore, this last route of production of capsorubin also leads to an exploitation of the chemical industry. To this are associated is all the consequences of a need of a semi-synthetic product on the market (in particular for the most demanding groups) and the environmental impact to produce it.

The major problem of carotenoid production from vegetables is the high cost, due to the long and complicated extraction procedures, and the low yield. In fact, for example, to obtain 2 grams of carotene it is necessary to process about 50 kg of carrots. In contrast, the chemical synthesis of carotenoids can produce only some naturally occurring carotenoids of about 700 (Bogacz-Radomska and Harasym 2018, doi: 10.1093/fqsafe/fyy004). As regards the specific case of capsorubin, there is currently no method for its specific extraction. The present methodologies related to pepper carotenoids are exclusively aimed at carotenoid capsanthin with a yield between 15% and 50% (CN1740236A).

SUMMARY OF INVENTION

The object of the present invention is to provide a process which allows to obtain chromoplastid carotenoids with a very high yield and with a purity higher than 70%, higher than 80%, higher than 85%, higher than 90%, higher than 96%.

The carotenoids thus obtained can be formulated in compositions for dietetic, pharmaceutical, nutraceutical and cosmetic applications.

The process of the invention is based on the isolation of a suspension of homogeneous fragments of the chromoplastidial membranes from the fruits. As an example, the actual procedure is described on the chromoplastidal membranes of *Capsicum annuum* (common red pepper) which, after isolation, are at first solubilized by alkyl-saccharidic and alkyl-thio-saccharidic detergents, and then screened, for example by size exclusion chromatography (SEC—Size Exclusion Chromatography). This procedure allows the direct and high-purity isolation of the carotenoid of interest, in this case the capsorubin, which is isolated in the form of regular aggregates in shape and size.

As a result high levels of purity are obtained, comparable to the procedure (b) mentioned in the paragraph "prior art" with costs (low) and quantities (high) comparable to the procedure (a) mentioned in the same paragraph.

Further purposes will become apparent from the following detailed description.

DETAILED DESCRIPTION

Figure 1:
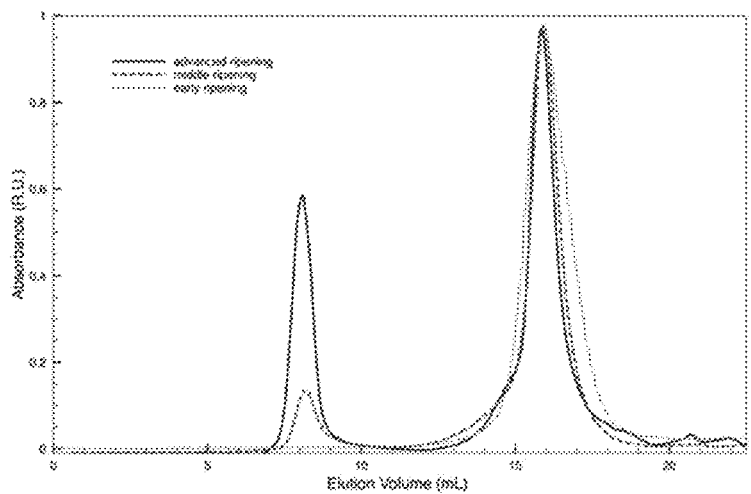
FIG. 1: Comparison of the levels of regular carotenoid aggregates during the ripening of *Capsicum annuum* fruits. The chromatographic graphs show 3 different stages of ripening as first stages of ripening, intermediate stages of ripening, phases of complete ripening. The graphs were normalized with respect to the protein peak (rest of the solubilized material) visible around 15-17 mL. The peak of regular carotenoid aggregates is visible in the range between 7 and 9 mL.
Figure 2:
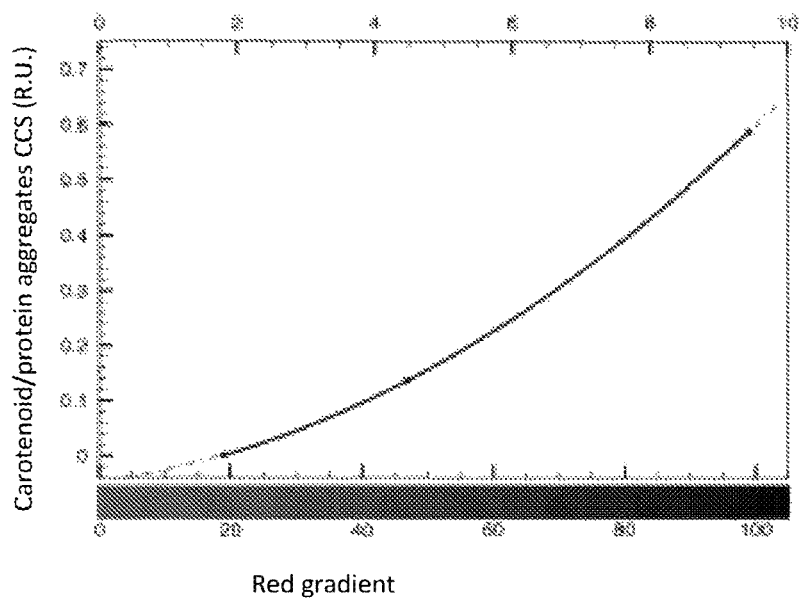
FIG. 2: Trend of accumulation of carotenoid aggregates with respect to time and level of pigmentation/fruit ripening (red shade).

The invention relates to a process for obtaining chromoplastid carotenoids that can be isolated from plants, in particular plant's fruits. Aschromoplastidcarotenoids we mean all carotenoids that, under different forms (free, associated with sugars, or associated with proteins), are accumulated in plastid organelles typical of fruits and called chromoplasts. Within the long list of carotenoids that can be found in chromoplasts, depending on the type of fruit, there can be found: capsorubin, lycopene, carotenes (-α, -β, -γ) and xanthophylls such as zeaxanthin, violaxanthin, and lutein.

More in detail, the process according to the invention allows to selectively isolate the carotenoid (such as capsorubin) in the form of aggregates, regular in shape and size on the basis of the size (Size Exclusion Chromatography) and in pure form. The process includes the following steps:
  i) production, in suspension, of homogeneous fragments of chromoplastidial membranes from fruits, such as for example the fruits of *Capsicum annuum* (common red pepper) in a temperature range of 4-20° C. and a pH range between 5 and 7;
  ii) solution isolation of the membrane components by solubilization with detergents in a temperature range of 4-20° C. and a pH range 5 to 7;
  iii) selectively and in high purity isolation of the carotenoid in the form of regular paracrystalline aggregates using a screening technique such as size exclusion chromatography (SEC—Size Exclusion Chromatography) or alternatively ultracentrifugation (at least 35,000 g for 10' at 4° C.), or alternatively by filtering membranes with a cutoff lower than the weight of the carotenoid aggregates and therefore less than 500,000 daltons, weight ascribable to the operating intervals of the nano- and ultrafiltration membranes (4000 g for 60' at 4° C.). In the filtering membranes the aggregates are separated by size exclusion (4000 g for 60' at 4° C.). In the case of ultracentrifugation, sucrose gradients are used, or percoll or equivalent, which separate the components of the sample present in the medium, in our case the carotenoid aggregates, by sedimentation thanks to density difference. Instead in the case of the filtering membranes the aggregates are separated by size exclusion (4000 g for 60' at 4° C.).

This procedure is carried out at subacidic pH (pH 5-7), typically in a buffered environment, for example with phosphate buffer, at a temperature between 10° C. and 18° C., and at atmospheric pressure with the sole exception of the last step (iii) which occurs at pressures up to 2 MPa, according to the operating conditions of the SEC.

Step (i) is carried out substantially in accordance with the methods known in the literature developed by the authors themselves (for example by following what reported by Piano D. et al. (2010); Photosynth. Res. 106 (3): 221-6, Farci D. et al. (2016), J Exp Bot. 67: 3303-3312; Collu G. et al. (2017), Plant Mol Biol. 94: 125-136).

The fruits are washed, cut into pieces and finally the tissues are fragmented mechanically. The suspension, typically obtained in a ratio of at least 1:1 or lower (w/w) in buffered water (50 mM phosphate buffer pH 5.0-7.0), is subjected to centrifugation to eliminate the water-soluble cytosolic fraction. This step is carried out in a temperature range of 4–20° C. and a pH range 5 to 7 in a buffered environment, typically with 50 mM phosphate buffer.

In Step (ii), the solid fraction separated by centrifugation is resuspended in water, typically water buffered to pH 5-7 (for example 50 mM phosphate buffer, pH 7) typically in a weight ratio of at least 1:1 or lower (w/w), depending on the sample. The suspension thus obtained is homogenized, for example by means of 2-6 cycles with glass or steel piston homogenizers. After homogenization, the detergent is added and the solution is solubilized for 5-30 minutes by adding detergents under slow stirring and in the dark. Alkyl-saccharidic and alkyl-thio-saccharidic detergents are used, respectively of general formula:

in which:
  m=integer between 1 and 2;
  X=O or S;
  M=chosen from aldoses and ketoses and relative mixtures;
  R=$C_6$-$C_{15}$ linear or branched alkyl chain, preferably $C_7$-$C_{13}$, more preferably $C_8$-$C_{12}$.

Detergents from the group of alkylmaltosides or alkylglucosides are preferred.

The saccharidic and thiosaccharidic detergents are known and marketed by Sigma Aldrich, Thermofisher, Anatrace (https://www.anatrace.com/Products/Detergents) and can be used individually or in mixture with each other.

However, other mild detergents can also be used efficiently.

The saccharidic detergents have the ability to maintain the regular aggregates of carotenoids in their "native" state, i.e. in the form in which they are found in vivo, preventing denaturation, even at high concentrations (3-5%), of the supramolecular structures that we call regular aggregates.

If a traditional detergent such as Sodium docecylsulfate (SDS) were used instead of the saccharide detergent, there would be a complete denaturation of the supramolecular structures of the carotenoid, making this procedure vain. As a matter of fact, through the process of the invention the denaturation of the separated aggregates is prevented.

The choice of the type of detergent and its quantity depends on the composition of the chromoplastidial membranes, which in turn depends on the quality and the ratios of the different lipid components present in the membranes of the considered plant species. In particular, the greater the lipid component, the greater the amount of detergent to be added. The person skilled in the art, by using his own knowledge and the teachings of the present invention, is able to choose the most suitable detergents and determine the optimal quantities, bearing in mind that the use of detergents in the -tio forms provides a further increase in the aggression.

Following the addition of the saccharidic detergent, the cell membranes are solubilized, that being liposoluble, are kept in solution incorporated in the detergent micelles. The membrane protein systems and all the components associated with the membranes, including carotenoids, are also solubilized.

The thus obtained suspension is subjected to a further centrifugation step which allows the fraction containing the carotenoid object of the present invention to be isolated in solution.

In step iii) the isolated component in solution during the previous phase is subjected to screening to separate the pure carotenoid. For example, a chromatographic column for size exclusion (SEC) of dimensions proportional to the volume of sample to be loaded and to the amount of starting fruit can be used (approximately 100 m of fruit requires approximately 10 mL of chromatographic resin to separate the carotenoid). Through this phase the separation and isolation in high concentrations and purity of the carotenoid will occur. The separation procedure is carried out on a resin composed of agarose and dextran beads, such as Superdex 200, in the temperature range between 4° C. and 20° C. in 50 mM phosphate buffer and an optimal pH range 7.4, but in a possible range that goes from pH 6 to 8, with an efficient separation. The separation is carried out at a flow rate of 0.5-1 mL/min with elution of the subject carotenoid at 7-8 mL on columns of 24 mL and with a diameter of 30 mm. However, these elution values will vary according to the type of fruit considered and therefore to the type of carotenoid subjected to isolation. In general, carotenoid aggregates are eluted at volumes corresponding to 500,000 dalton.

Carotenoid aggregates appear as molecular H-type aggregates, where carotenoid molecules organize themselves like side-by-side stacks inside the aggregate through hydrogen bonds.

Typically, the molecular weights of the aggregates can range from 10,000 to 600,000 dalton.

The possibility of exploitation of the present method originates from the property of capsorubin, a property identified following the research activity of the proponents, of forming organized structures of pure carotenoid with univocal mass and shape. This property has been identified in pepper, but similar carotenoid organizations have been identified in other fruits such as lycopene in tomatoes. An example of purity separation is shown in FIG. 1 which also shows the greater amount of carotenoid in fruits in an advanced state of ripeness. This last aspect makes the peppers no longer marketable (e.g. in the large-scale retail trade) recoverable and exploitable for the production of a final product of high commercial value. The product obtained through the procedure described here allows to obtain large quantities of carotenoids in high purity that can be used both in the therapeutic field for pathologies involving or resulting in a state of cellular oxidative stress (tumors, metabolism alterations, neurodegenerative pathologies), and in nutraceuticals as food supplements, and in cosmetics for the production of anti-aging creams and "make-up" cosmetics (lipsticks, blushes, eye shadows and the like) with both a coloring and a protective function against sunlight.

The carotenoids obtained with the process of the invention can be combined with excipients and also with other pharmaceutically, cosmetically or nutraceutically acceptable active ingredients for making food, pharmaceutical and cosmetic compositions.

The compositions can be formulated in liquid or solid form for oral, parenteral or topical assumption.

The procedure according to the present invention allows the isolation in a direct way and high purity of the carotenoid capsorubin and of all the carotenoids naturally accumulated in the chromoplasts as regularly shaped and sized aggregates.

As a result high levels of purity are obtained, comparable to the procedure (b) mentioned in the paragraph "prior art" with costs (low) and quantities (high) comparable to the procedure (a) mentioned in the same paragraph.

The "native" level of the carotenoid is maintained thanks to the use of mild detergents and this approach allows to exploit a discriminating factor that allows to separate the carotenoid in its untouched supramolecular organization. In this way, through this process it is possible to obtain a carotenoid in its naturally present form in the chromoplasts as no denaturation of proteins takes place.

I.e., the aggregate containing the carotenoid obtained by the process of the invention is substantially indistinguishable from a product obtained with traditional extraction, apart from the much higher yield and the much lower cost. The carotenoid extracted with the invention process is free from contaminants such as other carotenoids or solvents, whether they are polar or non-polar.

To the knowledge of the inventors, at present there is no patented procedure for the isolation of capsorubin and in general there are no known procedures to isolate carotenoids through the use of protein chromatography (FPLC—Fast Protein Liquid Chromatography) and in particular that of exclusion in size (size exclusion chromatography). Both techniques are known to the person skilled in the art. This fact implies the possibility of isolating large quantities of high-purity carotenoid very efficiently. This technique is opposed to the extraction techniques actually known and in use, which are not very efficient, with a strong impact, and which use solvents starting from vegetable or animal matrices.

As opposed to the known methods, the procedure described here allows the fast isolation, in high quantities and in a high degree of purity of the carotenoid capsorubin through chromatography by size exclusion.

Among the advantages associated with extracting capsorubin through the technique in question, the high purity and high extractive efficiency should be emphasized. Capsorubin has a market value of between 600-700 euro/mg and the procedure developed makes it possible to obtain 10 to 100 times more product for a given quantity of starting material.

Finally, not only the quantity of product obtained is greater, but the latter is also extracted in high purity and all through a single passage.

The following examples are provided to illustrate the invention and are not to be considered as limiting the relative scope.

Example of the Procedure Carried Out on Red and Yellow Pepper.

The fruits are washed in running water, the seeds are removed, and, optionally, the rest is cut into pieces. A quantity of buffered water (50 mM phosphate buffer pH 5.0-7.0) is added to a 1:1 ratio (w/w) to a quantity of broken fruit equal to 100 grams. The obtained mix is then blended in order to obtain a homogeneous suspension.

The resulting suspension is filtered through a gauze-cotton filter (a layer of cotton interposed between two layers of gauze) and the filtrate is centrifuged (4000 g×10' at 4° C.) in order to obtain the resulting solid fraction, consisting of the chromoplastidial membranes. The membranes are finally resuspended in buffered water. This step is followed by the isolation in solution of the membrane components by solubilization with mild detergents (preferably from the group of alkylmaltosides or alkylglucosides), in a pH range between 5 and 7. The whole procedure takes place in a temperature range of 4-20° C. After solubilization, the sample is centrifuged (4000 g×10' at 4° C.), the solid fraction eliminated while the fraction in solution is further processed to selectively isolate the carotenoid in the form of regular paracrystalline aggregates in high purity. This isolation is achieved through a screening technique such as size exclusion chromatography (SEC—Size Exclusion Chromatography) or alternatively ultracentrifugation, or alternatively nano- and ultrafiltration filtering membranes. The carotenoid thus obtained is characterized by UV-Visible spectroscopy, so as to identify the points of maximum absorption which are always characteristic and therefore traceable to a single carotenoid, and therefore useful for identifying the isolated carotenoid by the procedure described herein.

The invention claimed is:

1. A process for obtaining a chromoplastid carotenoid from a plant fruit comprising the following steps:
   i) preventive washing and crushing of the plant fruit;
   (ii) fragmenting mechanically the washed and crushed fruit in a first buffered solution;
   (iii) centrifuging to generate a water-soluble cytosolic fraction and a solid fraction to separate out the water-soluble cytosolic fraction;
   (iv) recovering the separated solid fraction comprising a chromoplastidial membrane after the centrifugation, and dispersion of the separated solid fraction in a second buffered solution,
   (v) adding to the second buffered solution having dispersed therein the separate solid fraction an alkylsaccharide detergent, thereby solubilizing the chromoplastid carotenoid, and mixing and subsequent centrifuging to generate a supernatant solution; and
   (vi) removing the supernatant solution after the centrifugation of step (v), and
   (vii) isolating the chromoplastid carotenoid from the removed supernatant solution by a process selected from the group consisting of: Size Exclusion Chromatography, Fast Protein Liquid Chromatography, ultracentrifugation, nano- and ultrafiltration.

2. The process of claim 1 wherein in step (iii), the solid fraction separated by centrifugation is resuspended in buffered water at between about pH 5-7 in a weight ratio of at least 1:1 or lower (w/w) to generate a suspension, and the suspension thus obtained is homogenized and solubilized for between about 5-30 minutes by adding detergents under slow stirring and in the dark.

3. The process according to any one of claim 1, wherein the alkylsaccharidic detergent has the following general formula:

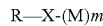

in which:
m=integer between 1 and 2;
X=0 or S;
M=selected from aldose and ketose monosaccharide groups and corresponding mixtures;
R=C6-C15 linear or branched alkyl chain.

4. The process of of claim 1, wherein the alkylsaccharidic detergent is selected from the group consisting of alkylmaltosides and alkylglucosides, taken individually or in mixture with each other.

5. The process of of claim 1, wherein the plant comprises a vegetable.

6. The process of of claim 1, wherein the isolated chromoplastid carotenoid comprises: capsorubin, lycopene, or a carotene.

7. The process of claim 5, wherein the vegetable comprises a pepper, optionally *Capsicum annuum*, a tomato, optionally *Solarium lycopersicum*, or a mixture thereof.

8. The process of claim 6, wherein the carotene comprises alpha-carotene, beat-carotene, gamma-carotene or a xanthophyll.

9. The process of claim 8, wherein the xanthophyll comprises a zeaxanthin, a violaxanthin or a lutein.

10. A process for separating a chromoplastid carotenoid from a plant material comprising the following steps:
    i) preventive washing and crushing of the plant material;
    (ii) fragmenting mechanically the washed and crushed plant material in a first buffered solution;
    (iii) centrifuging to generate a water-soluble cytosolic fraction and a solid fraction to separate out the water-soluble cytosolic fraction;
    (iv) recovering the separated solid fraction comprising a chromoplastidial membrane after the centrifugation, and dispersion of the separated solid fraction in a second buffered solution,
    (v) adding to the second buffered solution having dispersed therein the separate solid fraction an alkylsaccharide detergent, and mixing the resultant solution, thereby solubilizing the chromoplastid carotenoid,
    (vi) centrifuging the solution generated after missing in step (v) to generate a supernatant solution; and
    (vi) removing the supernatant solution after the centrifugation step (vi).

11. The process of claim 10, wherein the alkylsaccharidic detergent has the following general formula:

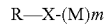

in which:
m=integer between 1 and 2;
X=0 or S;
M=selected from aldose and ketose monosaccharide groups and corresponding mixtures;
R=C6-C15 linear or branched alkyl chain.

12. The process of claim 10, wherein the alkylsaccharidic detergent is selected from the group consisting of alkylmaltosides and alkylglucosides, taken individually or in mixture with each other.

13. The process of claim 10, wherein the plant comprises a fruit.

14. The process of claim 11, wherein the fruit comprises a vegetable.

15. The process of claim 10, wherein the separated chromoplastid carotenoid comprises: capsorubin, lycopene, or a carotene.

* * * * *